United States Patent [19]

Slonina

[11] Patent Number: 4,704,120
[45] Date of Patent: Nov. 3, 1987

[54] HETEROTOPIC ARTIFICIAL HEART CONSISTING OF A ONE-PIECE CARDIAC PROSTHESIS FOR BIVENTRICULAR ASSISTANCE AND IMPLANTABLE IN THE RIGHT HEMITHORAX

[75] Inventor: Jean P. Slonina, Le Vesinet, France
[73] Assignee: Biomasys Sarl, Precy-sous-Thil, France
[21] Appl. No.: 878,139
[22] Filed: Jun. 25, 1986
[30] Foreign Application Priority Data Jul. 26, 1985 [FR] France ............................. 85 11431

[51] Int. Cl.⁴ .............................................. A61F 2/22
[52] U.S. Cl. ..................................................... 623/3
[58] Field of Search ........................................... 623/3
[56] References Cited

U.S. PATENT DOCUMENTS

| 3,518,702 | 7/1970 | La Russa . | |
|---|---|---|---|
| 4,576,606 | 3/1986 | Pol et al. | 623/3 |
| 4,578,077 | 3/1986 | Joh | 623/3 |
| 4,581,029 | 4/1986 | Joh | 623/3 |
| 4,588,404 | 5/1986 | Lapeyre | 623/3 |

FOREIGN PATENT DOCUMENTS 0143689 6/1985 European Pat. Off. .
2107724 5/1972 France .

OTHER PUBLICATIONS

IEEE Spectrum vol. 20, No. 3, Mar. 1983, pp. 39–44, M. A. Fischetti "The Quest for the Ultimate Artificial Heart".

Primary Examiner—Richard J. Apley
Assistant Examiner—James Prizant
Attorney, Agent, or Firm—Roland Plottel

[57] ABSTRACT

A one-piece prosthesis for biventricular cardiac assistance and reanimation is implanted in the right hemithorax between the diaphragm and the right lung symmetrically with respect to a diseased natural heart with which it operates in parallel. The prosthesis comprises a one-piece shell and two blood-circulating deformable-diaphragm pumps actuated by a compressed gas. The prosthesis face which rests on the patient's diaphragm is substantially flat and a substantially orthogonal face is provided with two ports for connecting the prosthesis to the natural heart while the other two connecting ports are inclined at an angle of 45°, connections between the ports and the natural heart being established by means of very short flexible hose elements. A system of port end-fittings serves to connect the prosthesis to the hose elements and to purge the prosthesis or to withdraw any air which may be present.

15 Claims, 27 Drawing Figures

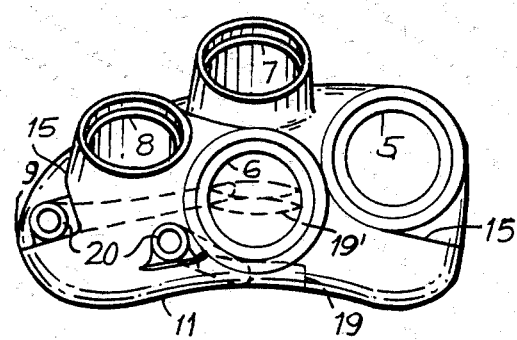
FIG. 3
FIG. 5
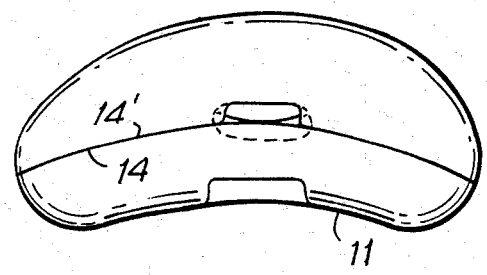
FIG. 4
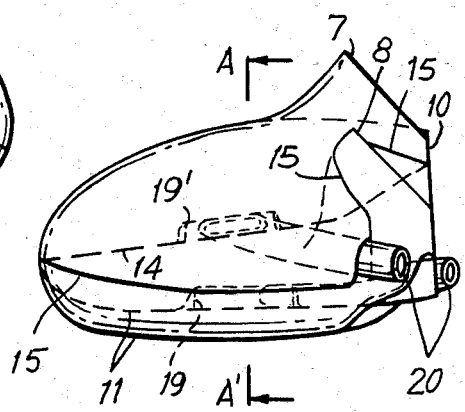
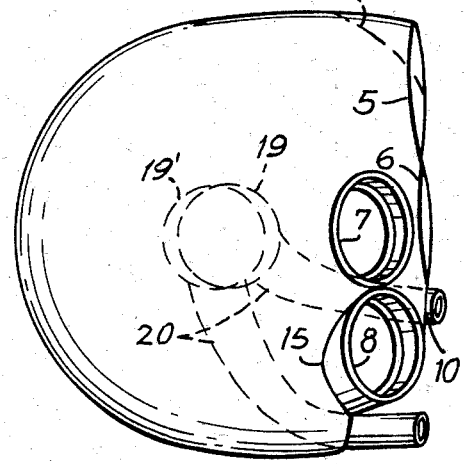
FIG. 6

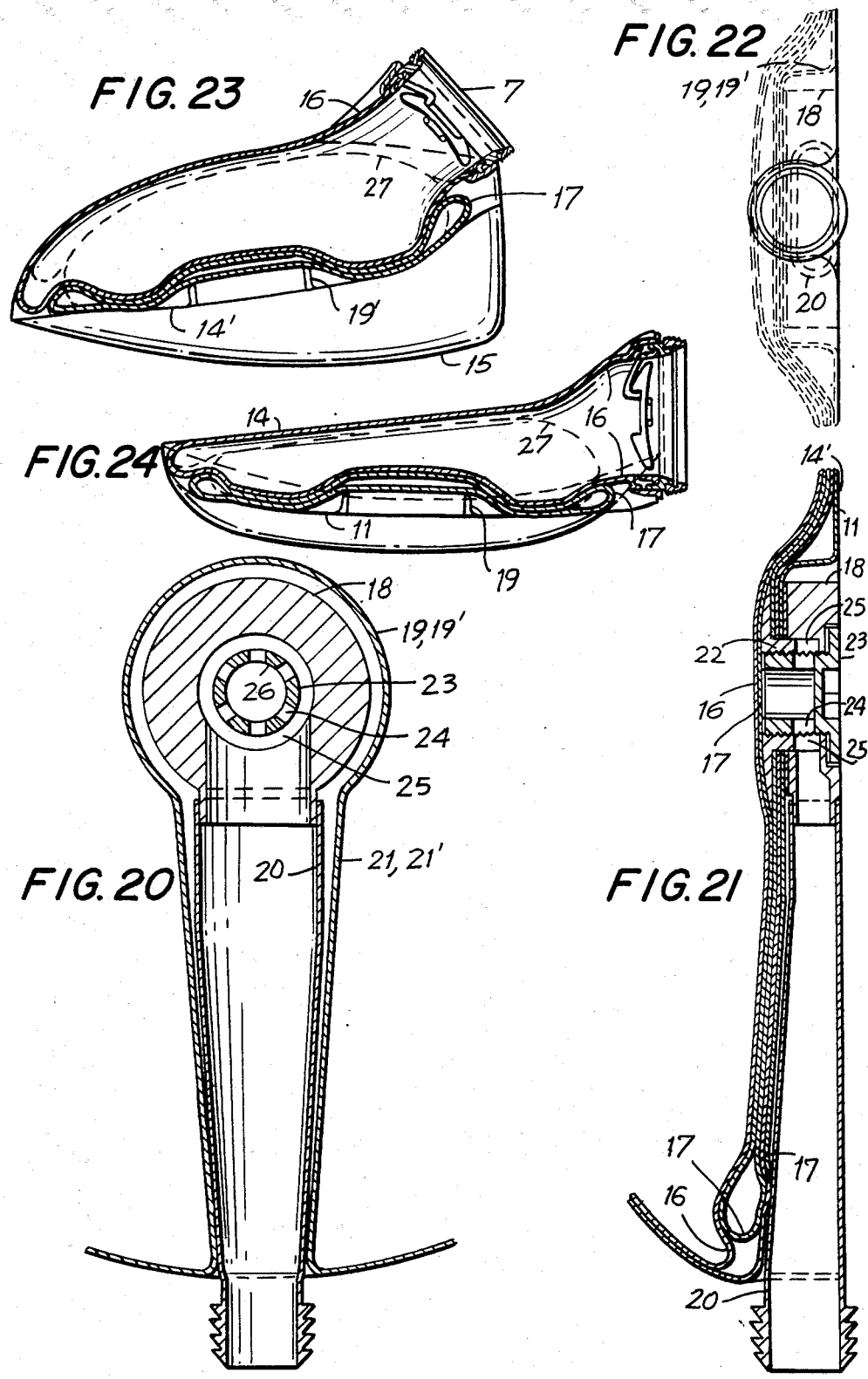

HETEROTOPIC ARTIFICIAL HEART CONSISTING OF A ONE-PIECE CARDIAC PROSTHESIS FOR BIVENTRICULAR ASSISTANCE AND IMPLANTABLE IN THE RIGHT HEMITHORAX

BACKGROUND OF THE INVENTION

1. Field of the Invention

The present invention relates to the field of equipment for reanimation and heart assistance. In more precise terms, the invention consists of a one-piece apparatus or satellite heart which is implanted surgically in the right hemithorax in order to assist the two ventricles of a diseased natural heart. This apparatus comprises two deformable-diaphragm pumps actuated by a compressed gas as well as means for connecting the pumps to the four natural blood vessels which communicate with the diseased heart.

2. Description of the Prior Art

The technique of cardiac transplantation in which a natural heart taken from a donor is grafted on a recipient has now been fairly well mastered and recent advances have resulted in an appreciable reduction of rejection phenomena. The practical application of this technique, however, remains relatively limited and fails to meet actual requirements by reason of the lack of natural heart donors.

For the reason just stated, it is an advantage to be able to assist the diseased heart of a patient by implanting a prosthesis in a patient's thoracic or chest cavity, this prosthesis being designed to operate in parallel with the natural heart which has remained in place, to assist the natural heart in its blood-pumping function and if necessary to perform a replacement function for any length of time in the event of failure of the natural heart.

Numerous examples of pumps for assistance of the left ventricle of the human heart are already known. The major disadvantage of this assistance technique is that it points to the additional need to assist the right ventricle.

Furthermore, the shape of left-ventricle assistance pumps which have already been developed is unsatisfactory from a physiological standpoint. Extrapolation of the techniques already employed to a left and right ventricle assistance pump would result in an apparatus which is even less physiological and therefore practically unimplantable in close proximity to the heart.

The aim of the invention is to produce a double cardiac assistance pump which is easy to use, which is efficient without giving rise to any serious disadvantage or inconvenience from the patient's point of view and which offers a high degree of reliability.

The cardiac prosthesis in accordance with the invention takes into account on the one hand the best location for implantation in the patient and on the other hand the best external shape which is compatible with this location and with a simple, effective and reliable technology of diaphragm pumps and connecting means.

The choice of the best location takes into account the following problems:

- The overall size of the prosthesis with respect to the organs which are located around this latter.
- The size of the artificial blood vessels or tubing employed for connecting the prosthesis to the natural blood vessels.
- The ease of attachment of artificial blood vessels to the natural blood vessels and of connection to the prosthesis.
- The need to ensure that the prosthesis does not interfere geometrically with the beats of the natural heart.

These conditions are satisfied by implantation of a prosthesis in accordance with the invention within the right hemithorax, that is to say between the muscular diaphragm and the right lung, and against the natural heart. The prosthesis proposed by the invention has a flattened and highly rounded general shape and is laid directly on the diaphragm. With respect to the human body, the satellite heart is symmetrical with the natural heart.

The symmetrical arrangement just mentioned is attended by the following consequences:

- The pumps for assisting the right heart and the left heart are directly connected to the right auricle and to the left auricle by means of two artificial blood vessels (hose elements) which are extremely short since the satellite heart is placed next to the natural heart.
- The pumps for assisting the right heart and the left heart are connected to the bottom end of the pulmonary artery and of the aorta respectively by means of two parallel ducts or so-called hose elements which are continuously in contact on the one hand with each other and on the other hand with the external wall of the pericardium. Thus the volumes occupied within the chest cavity are very small and pressure drops within the artificial blood vessels are minimized.
- The ports for admission and discharge of blood in the two pumps are located on the prosthesis face which is opposite to the natural heart at suitable angles in order to facilitate connection of said ports by the medical practitioner and to prevent either the artificial or the natural blood vessels from being subjected to any bending stress, tensile stress or shearing stress.

Blood-circulating pumps are of the flexible diaphragm type and are actuated by a fluid commonly consisting of compressed air, nitrogen or argon. The diaphragms are formed of hemocompatible polymer and especially of polyurethane. The ports of the pumps which are rigidly fixed to the prosthesis envelope are fitted with means for quick-action coupling to the artificial blood vessels, thereby facilitating the delicate operation of air-purging of the prosthesis.

SUMMARY OF THE INVENTION

In more precise terms, the invention relates to a one-piece prosthesis for biventricular heart assistance implantable in the right hemithorax beneath the right lung and placed on the patient's diaphragm symmetrically with the natural heart. Said prosthesis comprises a first blood-circulating diaphragm pump provided with two connecting ports attached by means of flexible hose elements respectively to the left auricle and to the aorta, and a second blood-circulating diaphragm pump provided with two connecting ports attached by means of flexible hose elements respectively to the right auricle and to the pulmonary artery, each port being fitted with a valve. The prosthesis in accordance with the invention is distinguished by the following features:

The shell in which said prosthesis is contained has a first substantially flat face adapted to bear on the patient's diaphragm and a second face located opposite to the natural heart and forming a substantially right-angled dihedron with the bearing face in the proximity of the ports, said second face being provided with two connecting ports, the shell being completed by a wall having a generally convex shape and provided with two other connecting ports which are inclined substantially at an angle of 45° with respect to said bearing face.

The prosthesis being placed horizontally on said first face and being viewed on said second face which is provided with the two ports for connecting said prosthesis to the auricles of the natural heart, said ports are so arranged that the port for connecting to the left auricle is located farthest to the right and that the port for connecting to the right auricle is located to the left of the port for connecting to the left auricle.

Pumping of blood is performed in the case of each pump by deformation of pouches of flexible hemocompatible material containing the blood, said deformation being produced by the external mechanical action of a compressed gas supplied by a device located outside the prosthesis.

BRIEF DESCRIPTION OF THE DRAWINGS

Other features of the invention will be more apparent upon consideration of the following description and accompanying drawings, wherein:

FIG. 3 is a side view of the prosthesis in accordance with the invention and looking on the face which carries the connecting ports;

FIG. 4 is a side view of the prosthesis looking on its front face or on the left end of the prosthesis shown in FIG. 3;

FIG. 5 is a sectional view of the prosthesis taken along a plane A—A' in FIG. 4;

FIG. 6 is a plan view of the prosthesis looking on its top face, or an overhead view of FIG. 4;

FIG. 20 is a sectional view of a duct for the supply of compressed gas to a gas-bladder ventricle, this view being taken in a direction at right angles to the flat bearing face of the prosthesis on the muscular diaphragm;

FIG. 21 is a side view of the gas supply duct of FIG. 20;

FIG. 22 is an end view of the same gas supply duct;

FIG. 23 is a sectional view of the left ventricle of FIG. 11 on a plane which passes through the axis of the aortic port;

FIG. 24 is a sectional view of the right ventricle of FIG. 8 on a plane which passes through the axis of the right-auricle port;

DESCRIPTION OF THE PREFERRED EMBODIMENTS

Figure 1:
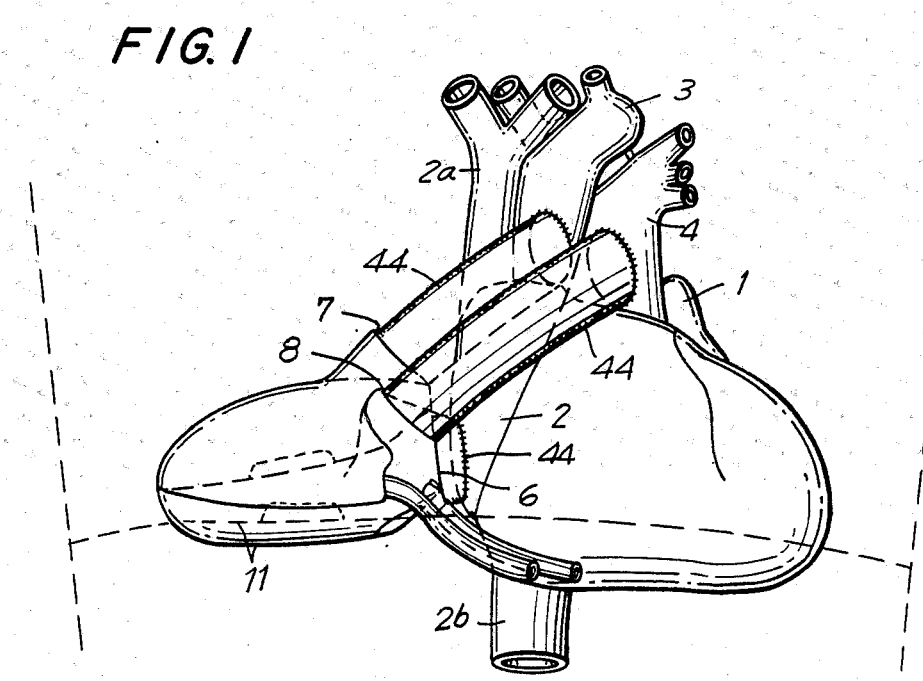
FIG. 1 is a view in elevation of an open chest or thoracic cavity showing the position of implantation of the heart assistance prosthesis in accordance with the invention and showing the connection of said prosthesis to the natural heart.
Figure 2:
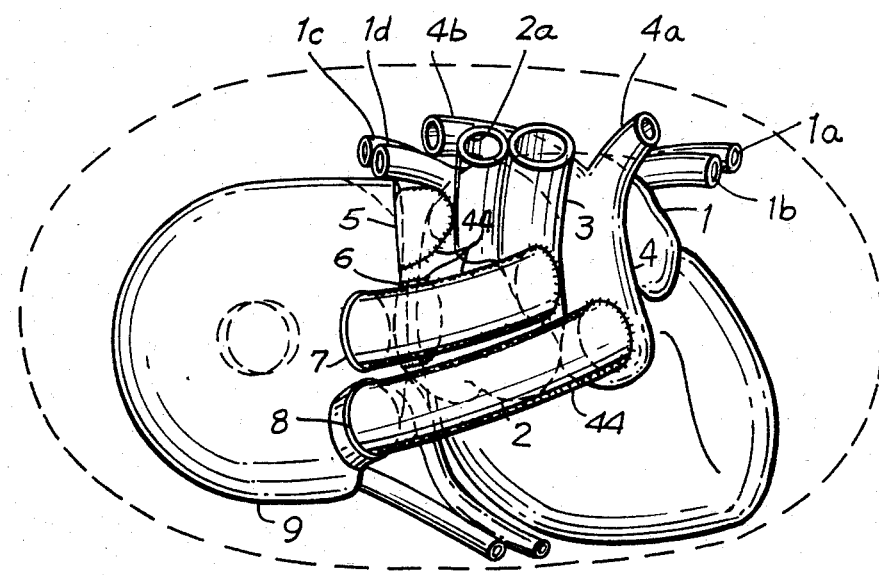
FIG. 2 is an overhead view of the open thoracic cavity which completes the preceding figure.

FIGS. 1 and 2 illustrate the implantation of the cardiac prosthesis in accordance with the invention within a patient's chest cavity, the chest cavity and diaphragm being shown in dashed lines. The choice of position-location of the prosthesis is defined by the criteria which have been set forth in the foregoing.

The shell of the prosthesis has a highly rounded and flattened shape in order to guard against any injury to or interference with the surrounding organs. The heart assistance prosthesis is placed on the patient's diaphragm in symmetrical relation with the natural heart.

The blood circulation ducts or vessels which terminate in the natural heart are the left auricle 1 with its left pulmonary veins 1a and 1b and right pulmonary veins 1c and 1d, the right auricle 2 with the superior vena cava 2a and inferior vena cava 2b, the aorta 3 and the pulmonary artery 4 with its left branch 4a and right branch 4b.

In regard to the ports of the heart assistance prosthesis, there are shown in these figures the ports for connecting the prosthesis to the left auricle 5, to the right auricle 6, to the aorta 7, to the pulmonary artery 8.

In FIG. 2, there can be seen the mode of access to the left auricle by the artificial blood vessel or so-called hose element 44 which extends from the port 5: an incision which is vertical with respect to the patient's body is made between the right pulmonary veins 1c and 1d and the right auricle 2, thus making it possible to attach a hose element 44 by stitching to the left auricle 1 with an oval cross-section having a vertical major axis. Access to the right auricle 2 takes place in the bottom right-hand portion of this latter directly in front of the prosthesis port 6. Access to the pulmonary artery 4 and to the aorta 3 takes place on their anterior or front face directly above the point of exit of these two blood vessels from the heart.

Taking into account these types of surgical access and the position of the ports 5 to 8 of the prosthesis, the total length of the artificial blood vessels or hose elements 44 has a value which is as small as possible. Moreover, the arrangement of the hose elements 44 leading to the auricles is such as to make them incollapsible and the arrangement of the hose elements 44 leading to the arteries is such that said hose elements are parallel and continuously applied against the heart, thereby minimizing their bulk for the right lung as well as their vulnerability. Furthermore, the path of the phrenic nerve for activation of the diaphragm is subjected to a minimum disturbance: it is only slightly displaced towards the anterior wall of the thoracic cavity.

Thus the essential advantages of this prosthesis are its geometry which is specifically adapted both to the physiology and to the anatomy of the patient. The prosthesis accordingly provides the natural heart with any required degree of assistance without affecting any possible chances of recovery of the natural heart since there is no interference with the cardiac function. Only the arteriovenous accesses of the natural heart are concerned, these accesses being provided solely by means of flexible hose elements which take up very little space. It may therefore be considered that this apparatus provides a temporary method of circulatory reanimation. It will be readily apparent that, since its internal technology guarantees high reliability, the apparatus is also capable of operating within a patient over long periods of time.

In order to ensure good adaptation to its position of implantation on the patient's diaphragm, that is to say between the muscular diaphragm and the bottom face of the right lung, the prosthesis has a flattened and rounded shape. The bottom wall 11 which is intended to rest on the diaphragm is sligntly incurved as shown in the drawings. This shape is intended to permit better adaptation to the diaphragm since this latter is convex at the location considered. However, the invention is not limited to this incurved shape. Said bottom wall 11 may thus have any convex or concave shape which is nearly flat or alternatively a plane surface without thereby departing from the scope of the invention. These particular considerations are necessary in order to explain the term "substantially flat" employed in claim 1.

In contrast, the top face located opposite to the face 11 is always convex.

Although the anterior face 9 of the prosthesis usually bears only on the right lung, it is also intended to bear on the internal wall of the chest cavity if the need arises.

On account of this external shape, the ventricles are arranged as shown in FIGS. 4 and 5. The diaphragm pump which performs the function of a right heart-assistance ventricle is placed in a flat position directly on the internal face of the wall 11. The top surface 14 of said pump which is opposite to the wall 11 is convex and serves as a support for the bottom face of the pump which performs the function of a left heart-assistance ventricle. The top surface of the left ventricle is the top wall of the prosthesis, namely the wall opposite to the wall 11. Thus in a sectional view of the prosthesis from the face on which the four ports 5 to 8 are located, the wall 11 being horizontal, the left ventricle is seen to have the shape of a crescent having tips which are directed towards the wall 11 and at equal distance from this latter.

This arrangement of the ventricles is an additional advantage of the invention since the pump diaphragms have a large surface area, thus permitting a smaller range of displacement in respect of the same pumped volume and consequently a lower degree of mechanical fatigue of the elastomers which constitute the pump diaphragms.

FIG. 3 shows the arrangement of the ports which provide accesses to the two pumps of the prosthesis.

The ports 5 and 6 are located on the wall 10 of the prosthesis in the same plane which is approximately perpendicular to the bottom wall 11 and have the function of connecting the prosthesis to the auricles. The ports 7 and 8 for connecting the prosthesis to the arteries are located in planes which are inclined to the wall 11 substantially at an angle of 45° with respect to this latter and are in contact with the wall 10.

The connection of the flexible hose elements 44 to the ports 5 to 8 of the prosthesis will hereinafter be described with reference to FIGS. 13 to 17.

The method adopted for pumping blood by means of the heart assistance prosthesis is essentially based on deformation of a flexible pouch containing the blood, said pouch being fitted with an inlet valve and with an outlet valve. Deformation is obtained as a result of action produced by an external gas pressure either directly on the external face of the membrane of the blood pouch or as a result of action produced by the external wall of a second membrane or diaphragm for retaining the gas.

Compressed gas is supplied to the prosthesis by means of two flexible tubes connected to the rigid end-pieces of the tubes 20, namely one flexible tube per ventricle. The method employed for supplying compressed gas to the prosthesis does not come within the scope of the invention but can be carried out by means of a compressor integrated within the patient's body or located outside the body. In this case, the flexible tubes pass through the chest wall or through the abdominal wall by means of a known system which prevents bacterial ingress.

The cardiac prosthesis in accordance with the invention is controlled and regulated in dependence on a known system based on the general principle of control of the heartbeat or rhythmic action of the heart in dependence on the venous return pressure, the physiological function of the heart being to discharge the blood which it receives and not to provide for the requirements of the human body. The control system also determines the two-thirds/one-third distribution of the diastole and systole periods and detects the increase in gas pressure corresponding to the end of systole. All of these functions are taken into account by the devices at present available for generating compressed gas for cardiac prostheses.

The beat rate of this prosthesis can also be readily synchronized with the natural heart rate by means of an electrode fixed in the natural heart. However, the experience which has been acquired up to the present time appears to show that synchronization of the beat rate of a heart assistance prosthesis with the rate of a very deficient natural heart under prosthetic assistance is subject to disadvantages which are liable to outweigh the advantages.

Reference being made to the set of FIGS. 3, 4, 5 and 6, the description given below will explain the general structure of the heart assistance prosthesis, the left and right ventricles of which are illustrated in detail in FIGS. 7 to 12.

The prosthesis comprises an outer envelope or so-called shell having the shape of a convex solid. A first substantially flattened characteristic face 11 of said shell constitutes the reference plane for the prosthesis and the face of this latter which bears on the patient's diaphragm. A second characteristic face 10 forms a dihedron with the first face and is provided with two of the four ports 5, 6, 7, 8 for connecting the prosthesis to the natural blood vessels. The face 10 of the dihedron in which are formed the ports 5 and 6 makes an angle which is substantially equal to 90° with the reference face 11. The ports 7 and 8 are in contact with the face 10 and their planes make an angle substantially equal to 45° with the face 10 and with the same reference face 11.

When looking on the prosthesis face 10 which is placed horizontally on the reference face 11, it will be apparent from FIG. 3 that the four ports are arranged as follows:

the port 5 for connecting the prosthesis to the left auricle is located on the extreme right-hand side.

The port 6 for connecting the prosthesis to the right auricle is located in a lower position than the port 5 and substantially at the midpoint of the width of the prosthesis.

The port 7 for connecting the prosthesis to the aorta is located above the port 6 and substantially at the center of the prosthesis.

The port 8 for connecting the prosthesis to the pulmonary artery is located to the left of the ports 6 and 7, substantially at the level of the port 5.

The relative positions of the ports 5 to 7 can also be defined as follows:

When looking on the second face 10 of the prosthesis which is placed on its bearing face 11, the port 7 which establishes a connection with the aorta 3 is located in the right half-plane of an oriented vector extending from the center of the port 5 for connecting the prosthesis to the left auricle 1 to the center of the port 6 for connecting said prosthesis to the right auricle 2.

This arrangement is completed by the fact that:

The ports 5 and 6 are located in a plane 10 which is substantially orthogonal to the reference plane 11.

The ports 7 and 8 are located in planes which make an angle of the order of 45° with the reference plane and enclose the prosthesis.

In regard to the two ventricles, the prosthesis being seen in the same position as the ports, they are constructed and arranged as shown in FIG. 5, namely as follows:

The right ventricle connected to the ports 6 and 8 has a substantially flat bottom face located against the internal wall of the face 11 and a top face 14 which is convex so that this latter meets the external envelope of the prosthesis at a substantially equal distance to the left and to the right of the face 11.

The left ventricle connected to the ports 5 and 7 has a concave bottom face 14' located against the top wall 14 of the right ventricle and a convex top face located against the internal wall of the upper portion of the envelope, with the result that the cross-section of said ventricle has the shape of a crescent, the tips of which are directed downwards at an approximately equal distance from the reference plane 11.

The construction of the cardiac prosthesis in accordance with the invention involves the fabrication of two independent external envelopes each containing one complete ventricle together with its diaphragm-type membranes and its compressed-gas supply tube.

Figure 7:
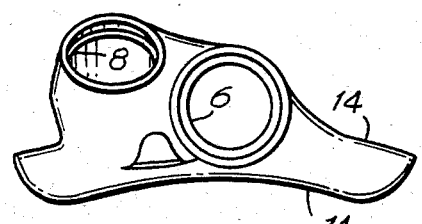
FIGS. 7, 8, 9 are views of the "right ventricle" of the prosthesis respectively on the face which carries the ports, on the front face and on the top face.

FIG. 7 illustrates the right or lower ventricle when looking on the face 10 described earlier. The bottom face 11 can be seen in the lower portion of the figure, the upper portion of which shows in outline the highest portion of the convex top wall 14. The ports 6 and 8 can also be seen.

Figure 8:
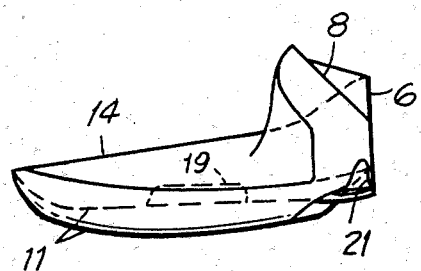
Figure 9:
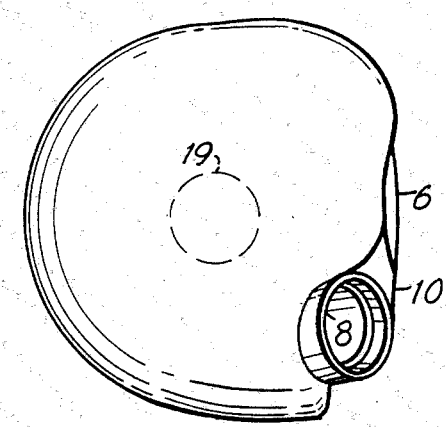

FIG. 8 is a side view of the same ventricle and FIG. 9 is a top view of FIG. 8.

Figure 10:
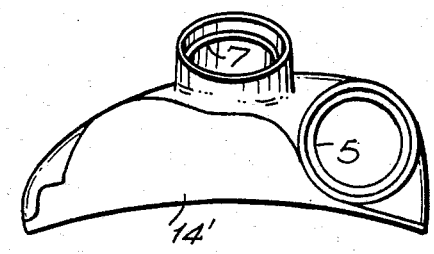
FIGS. 10, 11, 12 are views of the "left ventricle" of the prosthesis corresponding to the views of FIGS. 7, 8, 9.

FIG. 10 illustrates the left or upper ventricle when looking on the face 10. Apart from the ports 5 and 7 and their access zone, the general cross-section of this ventricle is designed in the shape of a crescent having downwardly directed tips as described earlier. The wall 14' is shown at the bottom of the figure and the external contour of the complete prosthesis is shown at the top of the figure.

Figure 11:
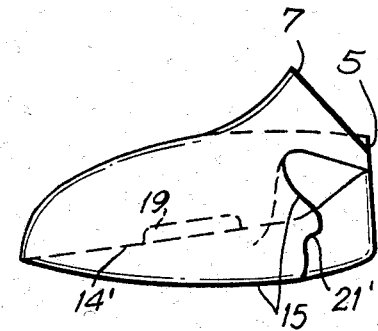
Figure 12:
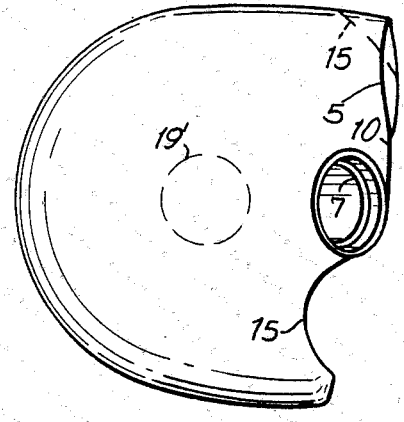

FIG. 11 is a side view of FIG. 10 and FIG. 12 is a top view of FIG. 11.

Although they are totally independent from each other and are in particular completely closed apart from their two ports and their gas inlet, these two ventricles are distinguished by the fact that, from a geometrical standpoint, they are designed to fit perfectly one within the other so as to reconstitute the complete prosthesis as defined in FIGS. 3 to 6. The line of junction of these two ventricles is indicated by the reference 15 in FIGS. 3 and 6 and does not designate any geometrical discontinuity. The line 15 is therefore the intersection of the faces 14 and 14' with the outer wall of the prosthesis.

The membranes (diaphragms) and the mode of activation associated with this embodiment are described in FIGS. 23 and 24 which are completed by FIGS. 20 to 22 for the supply of compressed gas.

In FIG. 23 which corresponds to FIG. 11 and is a cross-section taken along a plane which passes through the center of the port 7, there is shown a blood pouch 16 which is joined to the port 7 and a gas pouch 17 which is joined to a compressed-gas supply by means of the member 18. The blood pouch is formed of hemocompatible polyurethane. The member 18 is located within a compartment 19' formed in the wall 14'. FIG. 20 is an overhead view of this compartment together with the member 18 and its ancillary components. FIG. 21 is a side view of FIG. 20 and FIG. 22 is an end view of FIG. 21. The member 18 is joined by welding to a rigid tube 20 housed within a compartment 21' of semicircular cross-section which is joined to the circular compartment 19'. The tube 20 becomes increasingly flattened in shape as the member 18 is approached. The end portion of said tube 20 projects outwards from the prosthesis and is provided with means for attachment to a flexible gas-circulation pipe.

The gas pouch 17 is of one-piece construction, is totally closed except for its filling and attachment orifice, and is similar to a bladder by virtue of the fact that it has negligible inherent stiffness in the inflated state. It is for this reason that the pouch will hereinafter be designated as a gas bladder.

Said gas bladder 17, which is formed of elastomer, contains a metallic clamping head 22 which applies one of the walls of the gas bladder against the wall 14' in the zone located at the bottom of the compartment 19'.

Clamping is performed by means of the screw 23 which locks the bottom portion of the bladder 17 and the wall 14' between the head 22 and the member 18. Leak-tightness is ensured by means of seals. The flow of gas takes place within the circular groove 25 which is formed in the member 18 and feeds the radial bores 24 of the screw 23, thus making it possible to admit the gas into the bladder through the central bore 26.

It is apparent from FIG. 21 that the gas bladder 17 is provided in its zone of contact with the wall 14' with one or a number of additional thicknesses of elastomer 17' in order to maintain good stability during inflation and deflation by virtue of this local increase in stiffness but this latter does not, however, give rise to any stress concentration which would have a harmful effect on the elastomer.

In FIG. 24, which corresponds to FIG. 8 and is a cross-sectional view taken along a plane passing through the axis of the port 6, there are shown the same elements as those which are described with reference to FIG. 23. However, the shapes of said elements are adapted to those of the right or lower ventricle.

It is apparent from these figures that the air supply member 18 is identical for both ventricles but is located within the compartment 19' in the case of the left ventricle (therefore against the face 14') and within the compartment 19 in the case of the right ventricle (therefore against the substantially flat face 11).

The point of connection with the flexible tubes for the external supply of compressed gas to the rigid tube 20 of each ventricle is located at the outlet (outside the envelope) of the compartments 21 and 21' of semicircular cross-section. The locations can be seen in FIGS. 3 to 6. Other locations are possible without any need to modify the technology hereinabove described since the locations shown do not imply any limitation of the invention.

In FIGS. 23 and 24, the blood pouches are illustrated in the full state and all the valves are closed, namely the valve in the arterial discharge position in FIG. 23 and the valve in the venous admission position in FIG. 24.

The position of the blood pouches in the empty state is shown at 27. The valves illustrated schematically in these figures are commercially available and are not considered in any sense by way of limitation since many different types of commercial valves come within the scope of the invention.

The advantages of this mode of construction of the envelope coupled with this mode of activation of the diaphragm-type membranes are three in number.

In the first place, the possibility of forming the envelope of each ventricle without any welded joint or discontinuity in the bearing zone of the blood pouches, which is highly effective since any surface roughness is detrimental to fatigue strength. Assembly of the two ventricles is carried out either by means of external hooks or by welding or adhesive bonding of the faces 14 and 14' along their entire periphery or only at a few locations. The envelopes of each ventricle can be fabricated in a number of different ways. For example, one method consists of electrodeposition of a thin metal wall on a pattern which is fusible or soluble after the operation. The electrodeposited metals which are open to choice extend over a broad range but particularly worthy of mention are all the combinations of chromium, nickel, cobalt which are endowed in addition with relatively high biocompatibility.

Another method consists of molding with a plastic core or metals. Yet another method consists of spray-coating of plastic on a fusible pattern.

In the second place, the use of gas bladders for putting the blood under pressure makes it possible to obtain substantial general deformations without ever attaining high stress concentrations within the elastomer constituents as shown by the dashed lines 27 corresponding to maximum inflation of the gas bladders. On the contrary, if elastic membranes clamped on a rigid part are employed, the stresses are of higher value.

Finally, this mode of construction permits the achievement of significant cost savings.

Figure 25:
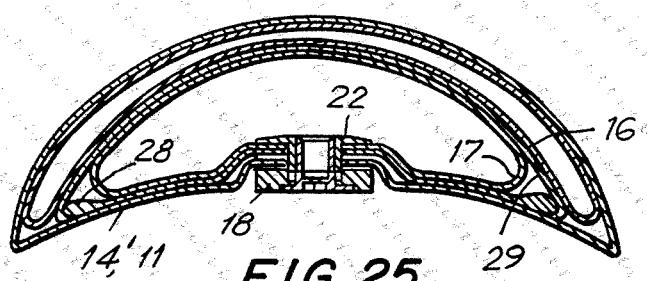
FIG. 25 is a sectional view of a gas-bladder ventricle provided with a net for limiting the range of displacement of the gas bladder, together with its anchoring plate.

This embodiment of the invention comprises a variant which is illustrated in FIG. 25.

It is in fact known that blood must not be repeatedly subjected to high local pressures since this would have the effect of impairing some of its constituents.

In order to control the beat rate of the prosthesis, it is in fact necessary to detect at the end of blood discharge and therefore of inflation of the gas bladder a discontinuity in the gas pressure curve arising from abrupt limitation in the increase in volume occupied by the gas. This consequently entails the need to subject the blood to a slight local overpressure since the limitation in volume increase of the gas bladder can be exerted only on the external face of the blood pouch 16. However, taking into account the total absence of roughness or irregularity of the internal surfaces of the envelope, the viscosity of the blood, the excellent distribution of pressure forces exerted by the gas bladder which has no inherent rigidity, and the high speed of detection of the final overpressure, it is highly improbable that such a slight traumatic action should subject the blood to any significant physical damage or destruction even over long periods of time.

However, if certain patients should exhibit signs of blood destruction after a very long period of operation of the prosthesis and if such signs should really be attributed to the phenomenon described in the foregoing and not to valve impact as is commonly found to be the case, one of the two solutions given below would accordingly be adopted.

Either retention of the pumping system described in FIGS. 23 and 24 but improvement of the control system so as to ensure that detection of discontinuity in the gas pressure curve indicating the end of discharge is in fact necessary only for a small fraction of the heartbeats, thereby reducing blood trauma in the same proportion.

Or modification of the pumping system described in FIG. 25.

A rigid plate 28 is inserted in the ventricle envelope by means of a limited cut made in the wall 14' or 11 according to the ventricle concerned. This plate 28 serves to anchor to the coupling sleeve a highly flexible but inextensible net 29 having a very fine mesh, only part of which is adhesively bonded beneath the plate 28, thus imprisoning the gas bladder 17. When all the parts 28, 29, 17 have been introduced within the module, the opening formed in the wall 14' or 11 is rewelded or re-bonded, depending on whether the envelope is of metal or of plastic material. During this operation, the assembly consisting of the parts 28, 29, 17 is not in contact with the wall 14' or 11, thus making it possible to heat the wall without involving any difficulty in regard to the organic products. The assembly is locked in position between the parts 22 and 18 together with seals and the situation is again the same as in the previous case.

By means of the net 29 which can be a self-lubricating woven fabric of very fine yarn, the gas bladder is locked in position at the end of its inflation travel without exerting any overpressure on the blood.

An alternative embodiment of the invention is described with reference to FIG. 26 which corresponds to FIG. 5 and with reference to FIG. 27 which corresponds to FIG. 4. The right or lower ventricle and the left or upper ventricle are arranged in the same manner as before but the two portions of the external envelope of the prosthesis do not correspond to each ventricle in particular. As shown in FIG. 27, the separation of the two portions of the envelope is a line 30 located in a plane parallel to the face 10 in the "maximum cross-section" zone of the prosthesis. This arrangement provides a relieved portion which is conducive to the introduction of rigid parts within the two portions of the prosthesis envelope. In order to close the two portions of envelope, it is possible to carry out edge-to-edge laser welding or electronic beam welding if the envelope is of metal or alternatively to perform welding or adhesive bonding over an overlap zone a few millimeters in width in the case of all suitable materials.

Figure 26:
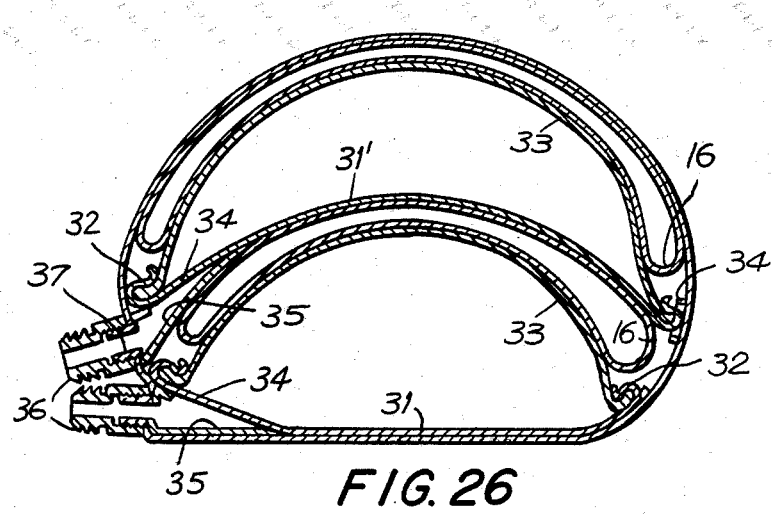
FIG. 26 is a sectional view of the cardiac prosthesis in the position of maximum expulsion of blood with a mode of activation of the blood pouches by means of diaphragms clamped in a rigid plate.
Figure 27:
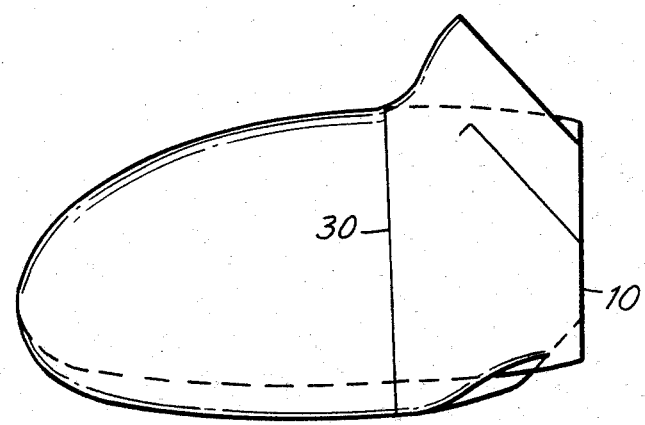
FIG. 27 is an external view of the prosthesis showing the position of the junction of the two portions of the external envelope when the mode of activation of FIG. 26 is adopted.

The pumping means introduced within the envelope in the case of each ventricle consists in this embodiment of a rigid plate 31 or 31', a diaphragm 33 being clamped in leak-tight manner by the rolled edge 32 or "curl" as shown in FIG. 26. Positioning of the plates 31 or 31' within the interior of the envelope is carried out by means of lugs or rails which are fixed on the envelope and in which the plate 31 or 31' is capable of sliding during its introduction within the envelope.

The gas diaphragms 33 have the function of compressing the blood pouches 16 which are of hemocompatible polyurethane as in the case of the pouches employed in the first embodiment. The diaphragm 33 can be inextensible, thus making it possible to obtain a very distinct signal indicating the end of a blood discharge. Said diaphragms may also be extensible, which permits better geometrical compatibility in the deflated position but produces a less distinct end-of-discharge signal.

The supply of compressed gas takes place through the hole 34 which is pierced in the plate 31 or 31' and through the curved plate 35 which determines a very flat leak-tight duct, said duct being welded to the hollow threaded end-piece 37 which passes freely through an opening of the outer envelope and is locked on this latter in leak-tight manner by means of a threaded union 36 fitted with a seal. The union 36 which is equivalent to the tube 20 of the first embodiment is also provided with means for attaching the flexible hose elements for external supply of compressed gas.

The connections between the blood pouches 16 and the blood vessels of the natural heart are established by means of the ports 5 to 8 of the prosthesis. Said ports are provided with end-fittings which can each be closed by a valve and to which the blood pouches 16 are connected within the interior of the prosthesis. Outside said prosthesis, one end of each flexible hose element 44 is connected to each end-fitting whilst the other end of each hose element is stitched to the corresponding auricle or artery of the natural heart.

The end-fittings mentioned in the foregoing are illustrated in detail in FIGS. 13 to 17. However, since there can exist a number of different designs of these end-fittings, those which are described below are not to be considered as a limitative aspect of the invention.

The end-fittings of the ports 5 to 8 permit unremovable fastening of the rigid coupling sleeves of the flexible hose elements 44 attached to the four natural orifices, this being achieved by employing in succession two types of clamping tools or so-called grippers.

Said end-fittings are designed to receive obturators which are capable of lateral displacement without hindering the coupling sleeves of the hoses in the pre-locking position of these latter. The housing of each obturator is closed by the coupling sleeve of each flexible hose element when this latter is in the fully locked position. By means of this system, it is possible to connect a prosthesis which has previously been filled with blood, thus avoiding any admission of air into the blood circulation system once the flexible hose elements have been subjected to an easy purging operation.

Attachment of the blood pouches 16 is carried out in the manner which will now be described.

A hollow cylindrical member 38 having a conical interior and a rounded bottom diametral constriction is welded or bonded within the orifice of the wall 10 which corresponds to the port 5, 6, 7 or 8 considered.

The blood pouch 16 is inserted through one of the two ports of the ventricle envelope, then partially passed out through the other port in order to place its two port admission and discharge ducts in a favorable position for their attachment.

A conical member 39 of stainless steel, titanium or polycarbonate is introduced into the interior of one of the cylindrical ducts providing access to the blood pouch 16, the function of said conical member being to expand the pouch elastically and to clamp its wall against the internal cone of the cylindrical member 38 as well as the bottom diametral constriction of this latter.

The valve 40 is then introduced and the end portion of the external cylindrical metal ring is applied within the interior of a bore formed within the member 39.

An annular member 41 of stainless steel, titanium or polycarbonate is then screwed into the cylindrical member 38 by means of a hook-spanner applied within radial holes (not shown) which are formed in its external accessible portion. Said member 41 thus exerts a continuous thrust on the cylindrical structure of the valve 40, on the member 39 and on the wall of the blood pouch 16 by counteraction, thereby achieving a high standard of leak-tightness.

Said annular member 41 is flared-out by a tube-expansion or drifting process, by rotary forging or by any other method of forging, in such a manner as to ensure that the portion of said member 41 which is located outside the prosthesis penetrates into, and is undetachably retained by, a recess formed by a groove 51 of an annular member 42 on which is fixed the end of a flexible hose element 44. The member 42 can be formed of the same material as the member 41, namely of hemocompatible metal or plastic material. Relative adjustment of the members 41 and 42 is such that the member 42 is capable of rotating with slight friction on the member 41. The degree of leak-tightness achieved by this assembly is sufficient for the blood by reason of its coagulability.

The annular member 42 can be shut-off by means of a plate 43 which passes radially through its wall on only one side and which is slidably mounted within a groove 52.

Figure 13:
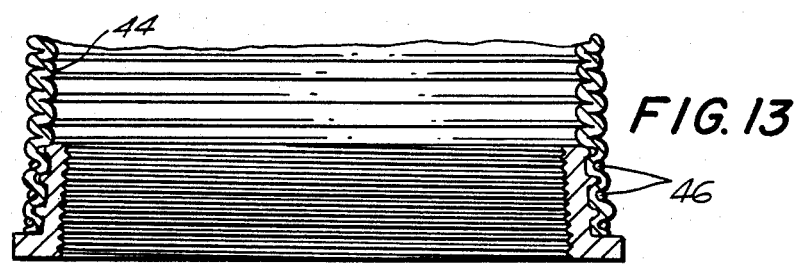
FIG. 13 is a sectional view of the flexible artificial blood vessel and of its rigid coupling sleeve.
Figure 14:
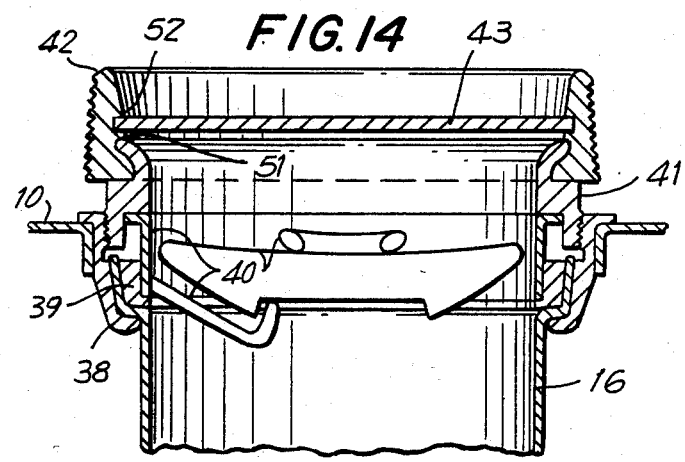
FIG. 14 is a sectional view of the complete assembly of one of the ports of the heart assistance prosthesis.
Figure 15:
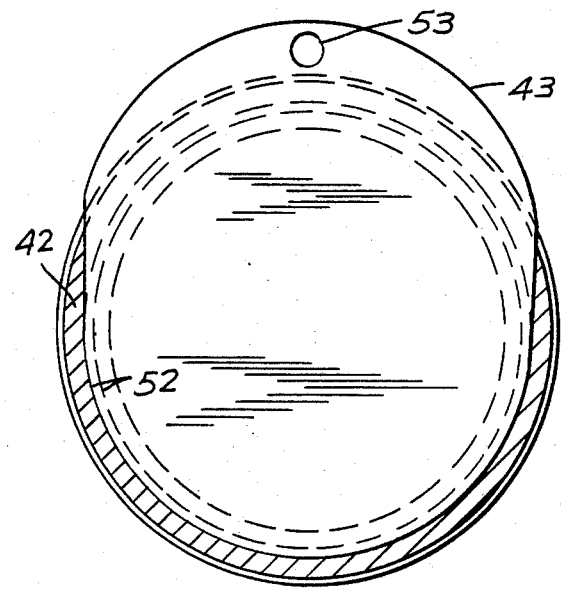
FIG. 15 is a sectional top view of the obturator shown in FIG. 14.

Moreover, the short textile hose elements 44 which the surgeon attaches by stitching at one end to the outlets of the four orifices of the natural heart each terminate at the other end in a rigid coupling sleeve 45 which is illustrated in FIG. 13. Each hose element is attached to its coupling sleeve 45 by means of a plurality of grooves which are formed in this latter and locked in position by means of independent circular threads 46. The hose elements 44 can also be secured to the sleeve 45 by stitching, this operation being performed by making use of radial holes formed in said sleeve.

The internal wall of the sleeve 45 is of frusto-conical shape and opens-out towards the prosthesis end-fitting to which it is intended to be connected by means of internal coupling teeth and grooves, these latter being adapted to cooperate with identical teeth and grooves formed on the frusto-conical external wall of the annular end-fitting member 42.

The design function of the plate 43 is to permit filling of the artificial heart with liquid, blood or physiological serum prior to implantation since air must not be allowed to pass into the patient's blood circulation system.

The final assembly of an end-fitting 45 on the body of the prosthesis after attachment to a natural blood vessel by stitching is shown in FIGS. 16 to 19. This assembly operation involves two steps. Each step calls for the use of an external clamping tool which is absolutely specific to the invention and will hereinafter be designated as a gripper.

Figure 18:
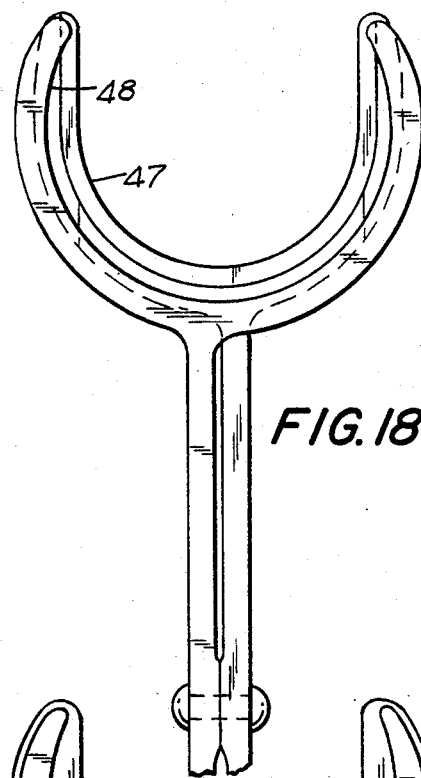
FIG. 18 is a plan view of the jaws of the gripper employed in FIG. 16.

In the first step, the lower fork 47 of a first gripper illustrated in FIG. 18 is introduced beneath the coupling sleeve 45. It will be noted that this lower fork has parallel sides. The hose element 44 is then introduced within the upper fork 48 of the gripper shown in FIG. 18. Said upper fork 48 has a contour in the shape of an interrupted circle. When a closing effort is exerted on the gripper, the fork 48 progressively surrounds the coupling sleeve 45, which is readily achieved since it is guided by the hose element 44. When the clamping position is reached, the coupling sleeve 45 is therefore necessarily located at a precise distance from the axis of the gripper. This precise distance combined with the fact that the fork 47 is fully inserted beneath the annular end-fitting member 42 and abuttingly applied against the member 41 permits error-free downward engagement of the coupling sleeve 45 around the member 42 in the pre-locking position.

This method of accurate position location is highly important since the surgeon has only poor visibility of this zone while he is performing the assembly operation.

Figure 16:
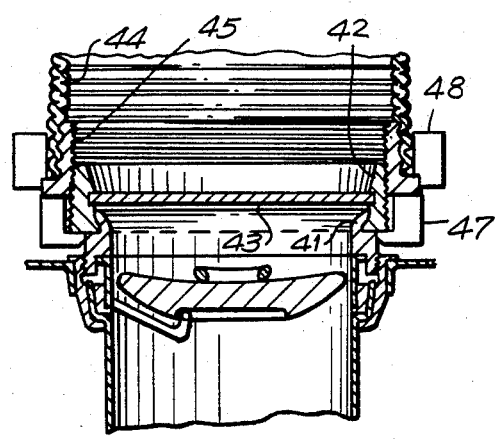
FIG. 16 is a sectional view of a flexible artificial blood vessel of the type illustrated in FIG. 13 in the pre-locking position on an end-fitting which is rigidly fixed to the heart prosthesis shown in FIG. 14, the gripper employed for the pre-locking operation being also shown in cross-section.
Figure 17:
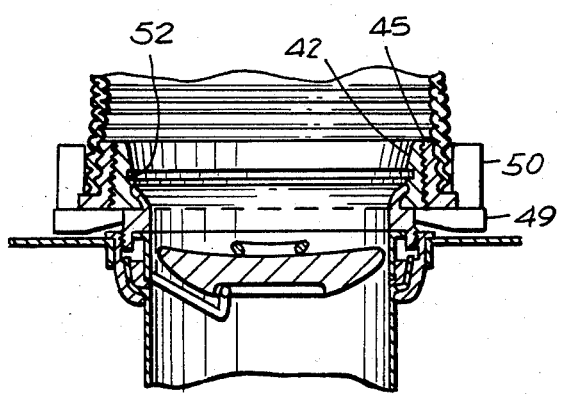
FIG. 17 illustrates the same elements as FIG. 16 in the final locking position, the gripper employed being also shown in cross-section.

After initiating downward engagement, the surgeon increases the effort exerted on the gripper, thus permitting snap-action engagement of the internal circular teeth of the coupling sleeve 45 in the external grooves of the end-fitting member 42 (as shown in FIG. 16). The radial thickness of the coupling sleeve 45 is in fact calculated as a function of the modulus of elasticity of its material (a metal such as stainless steel, titanium, or a plastic such as polycarbonate, for example) so as to permit a certain degree of circumferential elasticity and thus to permit snap-action engagement.

The surgeon can tighten the gripper to the maximum extent without danger since the fork 48 is applied against the fork 47 in such a manner as to ensure that the bottom end of the sleeve 45 does not quite come into contact with the sliding plate 43 and does not prevent subsequent ejection of this latter. The surgeon then opens the gripper to a sufficient extent to permit disengagement of the fork 48 from the sleeve 45 and finally withdraws the gripper.

After this initial attachment step, the surgeon carries out purging of the air contained in the hose elements 44, the flexibility of which makes this operation easy to perform.

Figure 19:
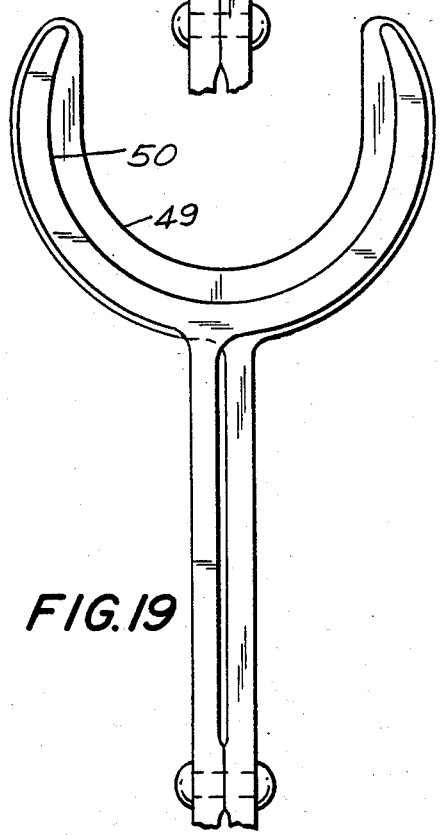
FIG. 19 is a plan view of the jaws of the gripper employed in FIG. 17.

In the second step of the assembly operation, the procedure is as follows:

The fork 49 of a second gripper shown in FIG. 19 is placed in position beneath the coupling sleeve 45. At the same time, the fork 50 is placed around the sleeve 45 without exert placed in position beneath the coupling sleeve 45. At the same time, the fork 50 is placed around the sleeve 45 without exerting any closing effort and simply rests on the sliding plate 43. The projecting portion of the plate 43 has previously been oriented towards the surgical access area, that is to say in the upward direction (the patient having been placed in a recumbent position), this being achieved by virtue of the possibility of rotational displacement with light friction of the end-fitting member 42 on the member 41.

The axis of the forks 49 and 50 is therefore oriented in a direction nearly parallel to that of the sliding plate 43. The surgeon introduces a small hook into the extraction hole 53 of the plate 43. He then exerts a pull on the plate 43 and ejects this latter, whereupon he immediately tightens his gripper. This tightening action causes the coupling sleeve 45 to slide over the end-fitting member 42 in the axial direction until it reaches the end of its travel. This movement of sliding displacement has the effect firstly of stopping the leakage caused by ejection of the sliding plate 43 and secondly of enhancing the clamping action of the sleeve 45 on the end-fitting member 42 by virtue of the two cooperating conical faces.

As will readily be understood, the invention is not limited in any sense to the embodiment hereinabove described with reference to the accompanying drawings and includes all equivalent technical means as well as any combinations which may be adopted without thereby departing either from the spirit of the invention or from the scope of the appended claims.

What is claimed is:

1. A one-piece prosthesis for biventricular heart assistance implantable in the right hemithorax beneath the right lung and placed on the patient's diaphragm symmetrically with the natural heart, said prosthesis being constituted by a first blood-circulating diaphragm pump provided with two connecting ports attached by means of flexible hose elements respectively to the left auricle and to the aorta, and a second blood-circulating diaphragm pump provided with two connecting ports attached by means of flexible hose elements respectively to the right auricle and to the pulmonary artery, each port being fitted with a valve, wherein:

the shell in which said prosthesis is contained has a first substantially flat face adapted to bear on the patient's diaphragm and a second face located opposite to the natural heart and forming a substantially right-angled dihedron with the adjacent bearing face in the proximity of the ports, said second face being provided with two connecting ports, the shell being completed by a wall having a generally convex shape and provided with two other connecting ports which are inclined substantially at an angle of 45° with respect to said bearing face;

the prosthesis being placed horizontally on said first face and being viewed on said second face which is provided with the two ports for connecting said prosthesis to the auricles of the natural heart, said ports are so arranged that the port for connecting to the left auricle is located farthest to the right and that the port for connecting to the right auricle is located to the left of said port for connecting to the left auricle, wherein:

pumping of blood is performed in the case of each pump by deformation of a pouch of flexible hemocompatible material containing the blood, said deformation being produced by the external mechanical action of a compressed gas supplied by a device located outside the prosthesis.

2. A prosthesis according to claim 1, wherein:

the second diaphragm pump which has the function of assisting the right ventricle of the natural heart and is connected to the two ports for coupling said prosthesis to the right auricle and to the pulmonary artery respectively is placed on the first bearing face and limited by a convex internal wall of the prosthesis, said convex wall being joined to the shell of the prosthesis symmetrically with respect to the bearing face which is taken as a reference plane and when said prosthesis is viewed on the face which is provided with the two ports aforesaid;

the first diaphragm pump which has the function of assisting the left ventricle of the natural heart and is connected to the two ports for coupling said prosthesis to the left auricle and to the aorta respectively is placed on the convex wall which limits the second pump, said first diaphragm pump being also limited by the wall of generally convex shape of the prosthesis shell.

3. A prosthesis according to claim 1 wherein, when looking on the second face of the prosthesis which is placed on the first bearing face thereof, the port providing a connection to the aorta is located to the right of the port providing a connection to the pulmonary artery.

4. A prosthesis according to claim 1 wherein, when looking on the second face of the prosthesis which is placed on the first bearing face thereof, the port for providing a connection to the aorta is located in the right-hand half-plane of a vector which joins the center of the connecting port for the left auricle to the center of the connecting port for the right auricle.

5. A prosthesis according to claim 1, wherein the means provided in the case of each pump for producing a deformation of the blood pouch consists of a gas bladder, said gas bladder being anchored in the prosthesis by means of its compressed-gas admission device which is housed within a compartment.

6. A prosthesis according to claim 5, wherein the diaphragm of the gas bladder has a local overthickness in the zone which surrounds the compressed-gas admission device, said overthickness being intended to increase the stiffness of the diaphragm.

7. A prosthesis according to claim 5, wherein the gas bladder is provided with means for limiting the expansion of said gas pouch, said means being constituted by a flexible and inextensible net which is clamped around its periphery by a rigid plate, said plate being maintained in a stationarily fixed position by the members employed for attaching the compressed-gas admission device.

8. A prosthesis according to claim 1, wherein the means provided in the case of each pump for producing a deformation of the blood pouch consists of a flexible diaphragm which is clamped around its periphery by a rigid plate.

9. A prosthesis according to claim 1, wherein the two pumps are functionally independent and each pump is contained within a separate envelope which is closed except for the connecting ports, the two envelopes of said two pumps being interengaged along the convex internal wall within the prosthesis so as to reconstitute the one-piece outer shell of said prosthesis without any geometrical discontinuity in the line of junction of said two envelopes.

10. A prosthesis according to claim 1, wherein each connecting port is provided with an end-fitting for establishing a connection between a blood pouch and a flexible hose element, said blood pouch being fixed in said end-fitting by clamping between a first conical ring which is rigidly fixed to the prosthesis shell and a second conical ring, said second conical ring being locked in position by means of a valve structure and by means of an annular member which is screwed into said first conical ring.

11. A prosthesis according to claim 10, wherein a ring of cylindrical cross-section is provided externally with coupling teeth and grooves and is fitted with slight friction on the annular valve-locking member, said cylindrical ring being capable of rotational displacement with respect to said annular member.

12. A prosthesis according to claim 11, wherein the cylindrical ring serves to maintain a plate which is slidably and removably mounted in a groove formed in the body of said cylindrical ring, the function of said removable sliding plate being to shut-off said ring in a radial direction.

13. A prosthesis according to claim 11, wherein the flexible hose elements for connecting said prosthesis to the natural heart are attached at the end nearest the prosthesis to a coupling sleeve provided on the internal face thereof with coupling teeth and grooves adapted to cooperate with the external coupling teeth and grooves of the cylindrical ring of the end-fitting.

14. A prosthesis according to claim 13, wherein the engagement of the coupling sleeve of a flexible hose element on the cylindrical ring of an end-fitting has a pre-locking position which is obtained by closure of fork jaws of a first gripper, a first fork jaw being applied beneath the cylindrical ring of said end-fitting whilst a second jaw is applied against the coupling sleeve of the flexible hose element in such a manner as to ensure that, in the pre-locking position, the coupling sleeve of the flexible hose element is abuttingly applied against said first jaw in proximity to the end-fitting obturation plate and also permits sliding displacement of said obturation plate within the cylindrical ring of said end-fitting.

15. A prosthesis according to claim 13, wherein the engagement of a flexible hose element on the cylindrical ring of an end-fitting has a locking position which is obtained by closure of fork jaws of a second gripper, a first fork jaw being applied beneath the cylindrical ring of said end-fitting whilst a second jaw is applied against the coupling sleeve of the flexible hose element in such a manner as to ensure that, when the obturating plate has been withdrawn, locking of the coupling sleeve of the flexible hose element on the cylindrical ring of said end-fitting has the effect of shutting-off the groove in which the obturating plate is slidably mounted in the cylindrical ring of said end-fitting, final attachment in the locked position being achieved by cooperation of teeth and grooves formed in said coupling sleeve and in said cylindrical ring.

* * * * *